(12) United States Patent
Chen et al.

(10) Patent No.: US 8,658,647 B2
(45) Date of Patent: Feb. 25, 2014

(54) INTEGRIN-LINKED KINASE INHIBITORS

(75) Inventors: Ching-Shih Chen, Upper Arlington, OH (US); Su-Lin Lee, Columbus, OH (US); Samuel K. Kulp, Hilliard, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 13/300,872

(22) Filed: Nov. 21, 2011

(65) Prior Publication Data
US 2012/0142702 A1  Jun. 7, 2012

Related U.S. Application Data (60) Provisional application No. 61/416,804, filed on Nov. 24, 2010.

(51) Int. Cl.
*A61K 31/496* (2006.01)
*C07D 403/10* (2006.01)

(52) U.S. Cl.
USPC ...... 514/252.13; 544/336; 544/358; 544/371; 548/373.1; 548/376.1; 514/247; 514/252.12; 514/406

(58) Field of Classification Search
USPC ............ 544/224, 358, 371; 548/356.1, 373.1, 548/376.1; 514/247, 252.13, 406
See application file for complete search history.

(56) References Cited

U.S. PATENT DOCUMENTS

| | | | | |
|---|---|---|---|---|
| 7,026,346 | B2 * | 4/2006 | Chen et al. | 514/406 |
| 7,576,116 | B2 * | 8/2009 | Chen | 514/406 |
| 7,687,481 | B2 * | 3/2010 | McElroy et al. | 514/94 |
| 8,039,502 | B2 * | 10/2011 | Chen et al. | 514/406 |
| 8,080,574 | B2 * | 12/2011 | Chen | 514/406 |
| 8,084,467 | B2 * | 12/2011 | Makriyannis et al. | 514/326 |

* cited by examiner

*Primary Examiner* — Golam M M Shameem
(74) *Attorney, Agent, or Firm* — Tarolli, Sundheim Covell & Tummino LLP (57) ABSTRACT

A number of compounds and use of the compounds in a method for treating or preventing cancer in a subject by administering to the subject a pharmaceutical composition including a compound of formula I or a pharmaceutically acceptable salt thereof are described.

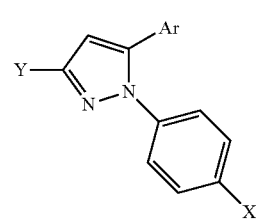

The compounds can also be used to inhibit integrin-linked kinase in a cell, which has an effect on the Akt signaling pathway.

17 Claims, 8 Drawing Sheets

INTEGRIN-LINKED KINASE INHIBITORS

CROSS REFERENCE

This application claims the benefit of U.S. Provisional Application Ser. No. 61/416,804, filed Nov. 24, 2010, the disclosure of which is incorporated by reference herein.

GOVERNMENT FUNDING

The present invention was supported by Grant Number R01 CA112250 from the National Center for Research Resources, funded by the Office of the Director, National Institutes of Health (OD). The Government has certain rights in this invention.

BACKGROUND

The Akt signaling pathway is an important regulator of multiple biological processes, such as apoptosis, cell proliferation, and metabolism. This pathway is frequently upregulated in human cancers through a number of different mechanisms, thereby promoting the survival of cancer cells and contributing to the clinical challenges of treating cancer patients. Complete activation of Akt requires phosphorylation at two amino acid residues: threonine-308 (T308), which is phosphorylated by phosphoinositide-dependent kinase 1 (PDK1), and serine-473 (S473), which is known as the PDK2 site and has been reported to be phosphorylated by a number of different kinases. One of these, integrin-linked kinase (ILK), has been identified as a promising anti-cancer target as its expression and activity are increased in various types of cancer, and its inhibition can suppress cancer cell survival by inducing apoptosis and cell-cycle arrest (Hannigan et al., Nature Reviews Cancer 5, 51 (2005)). The development of novel, potent, and safe inhibitors of ILK could provide new targeted therapeutics for the treatment of cancer.

The inventors have previously prepared a number of celecoxib derivatives for use as PDK-1/Akt signaling inhibitors, or for other applications. For example, U.S. Pat. Nos. 7,026,346 and 7,576,116 and Patent Publication No. 2008/0269309 describe a number of compounds useful as PDK-1/Akt signaling inhibitors and anticancer agents. U.S. patent application Ser. No. 12/428,035 by inventors describes a number of celecoxib derivatives that are useful for treating infection by *Francisella* bacteria.

Small-molecule inhibitors of ILK have also been reported. Among these, QLT0267 seems to have garnered recent interest as it has shown efficacy in preclinical studies (Kalra et al., Breast Cancer Res 11, R25 (2009); Eke et al., PLoS ONE 4: e6434 (2009); Edwards et al., Mol Cancer Ther 7, 59 (2008)). In breast cancer cells, the reported $IC_{50}$ values of QLT0267 for inhibition of cell viability ranged from 9.8-70.9 µM after 72 h treatment in vitro, and in vivo dosing via the oral or intraperitoneal routes required/used 100 or 200 mg/kg to suppress tumor growth in mice. However, there remains a need for additional ILK inhibitors, particularly those exhibiting high levels of activity.

SUMMARY OF THE INVENTION

The compounds of the present invention provide additional ILK inhibitors, and include a number of compounds exhibiting greater in vitro and in vivo potency than those previously known in the art.

In one aspect, the present invention provides a compound according to Formula I:

wherein Ar is selected from the group consisting of substituted or unsubstituted biphenyl, naphthyl, anthryl, and phenanthryl groups; Y is selected from the group consisting of sulfonamide, wherein n is an integer from 0-3, $R^1$ is H, methyl, ethyl, propyl, i-propyl, or benzyl; and $R^2$ is H, methyl or ethyl; X is selected from the group consisting of morpholine, guanidine, nitro, wherein $R^3$ is H, $SO_2NH_2$, L-Lys, D-Lys, β-Ala, L-Lue, L-Ile, Phe, Asp, Asn, Glu, or Gln and $R^4$ is H, methyl, ethyl, allyl, $CH_2CH_2OH$, or $CH_2CN$; or pharmaceutically acceptable salts thereof.

In another aspect, the present invention provides a method for treating or preventing cancer in a subject, comprising administering to the subject a pharmaceutical composition including a compound of formula I, as described herein, or a pharmaceutically acceptable salt thereof. In embodiments of the invention, the cancer can be leukemia, non-small cell lung cancer, colon cancer, central nervous system cancer, melanoma, ovarian cancer, renal cancer, prostate cancer, or breast cancer.

In a further aspect, the present invention provides a method of inhibiting integrin-linked kinase in a cell by contacting the cell with a compound of formula I, as described herein, or a pharmaceutically acceptable salt thereof.

DETAILED DESCRIPTION OF THE INVENTION

The inventors have developed a number of new compounds that can be used as integrin-linked kinase inhibitors and for treating or preventing cancer in a subject. These compounds are described by formula I, with the substituents defined in greater detail herein.

I

Definitions

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

As used herein, the term "organic group" is used to mean a hydrocarbon group that is classified as an aliphatic group, cyclic group, or combination of aliphatic and cyclic groups (e.g., alkaryl and aralkyl groups). An alkaryl group is a an aryl group that is attached to the remainder of the structure by an intervening alkyl group, whereas an aralkyl group is an aryl group that is attached directly to the structure but that includes one or more additional alkyl groups attached thereto. In the context of the present invention, suitable organic groups for the compounds of the invention are those that do not interfere with the desired activity of the compounds (e.g., their anti-cancer activity). In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., $C_1$-$C_4$ alkyl groups are alloy groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo moieties include chlorine, bromine, fluorine, and iodine.

The term "aryl" as used herein includes carbocyclic aromatic rings or ring systems. The aryl groups may include a single aromatic ring, a plurality of separate aromatic rings, or a fused aromatic ring system. Carbocyclic aromatic rings do not include heteroatoms. Examples of aryl groups include phenyl, naphthyl, biphenyl, fluorenyl and indenyl. Aryl groups may be substituted or unsubstituted.

Unless otherwise indicated, the term "heteroatom" refers to the atoms O, S, or N. The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "fused aryl group" includes fused carbocyclic aromatic rings or ring systems. Fused aryl groups include a plurality of aromatic rings that are fused to faun a single aromatic system. Examples of fused aryl groups include naphthalene ($C_{10}$), anthracene ($C_{14}$), phenanthrene ($C_{14}$) and pyrene ($C_{16}$) fused aryl groups. Collectively, fused aryl groups can be referred to by reference to the number of carbon ring atoms they contain; i.e., a $C_{10}$-$C_{18}$ carboaryl group.

The term "fused heteroaryl group" refers to fused aromatic ring systems including a plurality of aromatic rings that are fused to form a single aromatic system, in which one or more of the aromatic rings is a heteroaromatic ring. Fused heteroaryl groups are otherwise like fused aryl groups. Examples of fused heteroaryl groups include benzofuran, isobenzofuran, bezothiopene, indole, isoindole, $C_{10}$ heteroaryl groups derived from quinoline, isoquinoline, benodiazine, pyridopyridine, and $C_{14}$ heteroaryl groups derived from acridine and xanthenes.

When a group is present more than once in any formula or scheme described herein, each group (or substituent) is independently selected, whether explicitly stated or not. For example, for the formula —C(O)—$NR_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with one or more nonperoxidic O, N, S, or F substituents or other conventional substituents such as methyl groups. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

Additional substituents that can optionally be substituted on a group are further defined below.

Ester (carboxylate, carboxylic acid ester, oxycarbonyl): —C(=O)OR, wherein R is an ester substituents, for example, a $C_{1-7}$ alkyl group, or a $C_{5-20}$ aryl group, preferably a $C_{1-7}$ alky group (a $C_{1-7}$ alkyl ester). Examples of ester groups include, but are not limited to, —C(=O)$OCH_3$, —C(=O)$OCH_2CH_3$, —C(=O)O$(CH_3)_2$, —$(CH_2)_3$C(=O)$OCH_3$, and —C(=O)OPh.

Amido (carbamoyl, carbamyl, aminocarbonyl, carboxamide): —C(=O)$NR^1R^2$, wherein $R^1$ and $R^2$ are independently amino substituents, as defined for amino groups. Examples of amido groups include, but are not limited to, —C(=O)$NH_2$, —C(=O)$NHCH_3$, —C(=O)N$(CH_3)_2$, —C(=O)$NHCH_2CH_3$, and —C(=O)N$(CH_2CH_3)_2$.

Amino: —$NR^1R^2$, wherein $R^1$ and $R^2$ are independently amino substituents, for example, hydrogen or a $C_{1-7}$ alkyl group. Examples of amino groups include, but are not limited to, —$NH_2$, —$NHCH_3$, —NHCH$(CH_3)_2$, —N$(CH_3)_2$, —N$(CH_2CH_3)_2$, and —NHPh. Examples of cyclic amino groups include, but are not limited to, aziridinyl, azetidinyl, pyrrolidinyl, piperidine, piperazinyl, perhydrodiazepinyl, morpholino, and thiomorpholino.

Acylamido (acylamino): —$NR^1$C(=O)$R^2$, wherein $R^1$ is an amide substituent, for example, hydrogen or a $C_{1-7}$ alkyl group. Examples of acylamide groups include, but are not limited to, —NHC(=O)$CH_3$, —NHC(=O)$CH_2CH_3$, and —NHC(=O)Ph. Acylamido groups can be substituted; for example, the acylamido groups can be amine substituted acylamido groups having the formula —NH—CO—$(CH_2)_x$—$NH_2$, wherein x is an integer from 1-4.

Ureido: —N($R^1$)CONR$^2R^3$ wherein $R^2$ and $R^3$ are independently amino substituents, as defined for amino groups, and $R^1$ is a ureido substituent, for example, hydrogen or a $C_{1-7}$ alkyl group. Examples of ureido groups include, but are not limited to, —$NHCONH_2$, —NHCONHMe, —NHCONHEt, —$NHCONMe_2$, —$NHCONEt_2$, —$NMeCONH_2$, —NMeCONHMe, —NMeCONHEt, —$NMeCONMe_2$, —$NMeCONEt_2$ and —NHC(=O)NHPh.

Sulfonamide —S(=O)$_2$NRR$^1$, wherein $R^1$ is an amino substituent, as defined for amino groups, and R is a sulfonamino substituent, for example, a $C_{1-7}$ alkyl group or a $C_{5-20}$ aryl group. Examples of sulfonamide groups include, but are not limited to, —S(=O)$_2$NHCH$_3$, —S(=O)$_2$NHPh and —S(=O)$_2$N(Me)$_2$.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

Treat", "treating", and "treatment", etc., as used herein, refer to any action providing a benefit to a subject afflicted with a condition or disease such as cancer, including improvement in the condition through lessening or suppression of at least one symptom, delay in progression of the disease, prevention or delay in the onset of the disease, etc.

Prevention, as used herein, refers to any action providing a benefit to a subject at risk of being afflicted with a condition or disease such as cancer, including avoidance of the development of cancer or a decrease of one or more symptoms of the disease should cancer develop. The subject may be at risk due to exposure to a carcinogen, or as a result of family history.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

The present invention provides a number of compounds that can be used as anticancer agents or integrin-linked kinase inhibitors. These compounds can be described according to Formula I:

wherein Ar is selected from the group consisting of substituted or unsubstituted biphenyl, naphthyl, anthryl, and phenanthryl groups; Y is selected from the group consisting of sulfonamide, wherein n is an integer from 0-3, $R^1$ is H, methyl, ethyl, propyl, i-propyl, or benzyl; and $R^2$ is H, methyl or ethyl; X is selected from the group consisting of morpholine, guanidine, nitro, wherein $R^3$ is H, $SO_2NH_2$, L-Lys, D-Lys, β-Ala, L-Lue, L-Ile, Phe, Asp, Asn, Glu, or Gln and $R^4$ is H, methyl, ethyl, allyl, $CH_2CH_2OH$, or $CH_2CN$; or pharmaceutically acceptable salts thereof. The X, Y, and Ar substituents can all be varied independently from one another.

In some embodiments, the compounds of formula I include Ar as a biphenyl group according to formula II wherein $R^5$ is H, methyl, ethyl, propyl, isopropyl, tert-butyl, $CF_3$, $CCl_3$, hydroxyl, OMe, CN, $NO_2$, $NH_2$, $CONH_2$, CONHMe, acetate, $CO_2H$, $CO_2Me$, F, Cl, Br, or I. In some embodiments, $R^5$ is a haloalkyl group, such as a halomethyl group, while in further embodiments $R^5$ is a trifluoromethyl moiety ($CF_3$).

In further embodiments of the compounds of formula I, the Ar group is a fused aryl group. For example, the Ar group can be a naphthyl, anthryl, or phenanthryl group. The fused aryl groups can be attached to the remainder of the compound through any position along the ring.

In some embodiments, the Y substituent of the compound of formula I can be selected from sulfonamides, carboxamides (i.e., ), and esters (i.e., ), in which n is an integer from 0-3, $R^1$ is H, methyl, ethyl, propyl, i-propyl, or benzyl; and $R^2$ is H, methyl or ethyl. For example, Y can be In additional embodiments, the substituent X can be varied. For example, X can be selected from morpholine, guanidine, nitro, alkylamines

(i.e., )

and piperazines (i.e., ).

The group $R^3$ of the alkylamines can be H, $SO_2NH_2$, L-Lys, D-Lys, β-Ala, L-Lue, L-Ile, Phe, Asp, Asn, Glu, or Gln. In a preferred embodiment of the invention, the group $R^3$ is β-alanine. The amino acids of $R^3$ are bonded to the amine through their carboxyl moiety, forming an amide or "peptide" bond. The $R^4$ group of the piperazines can be H (providing piperazine), methyl, ethyl, allyl, $CH_2CH_2OH$, or $CH_2CN$.

Particular combinations of the substituents described above are used in additional embodiments of the invention. For example, an addition embodiment of the compounds of formula I provides Ar as phenanthryl, X as piperazine, Y as and $R^1$ as H, methyl, ethyl, propyl, isopropyl, butyl, or benzyl.

In a number of embodiments of the invention, the Ar group is a 4'-trifluoromethyl, 1,1'-biphenyl moiety, as shown below:

In embodiments in which Ar is the 4'-trifluoromethyl, 1,1'-biphenyl moiety, X is piperazine, Y is and $R^1$ is H, methyl, ethyl, propyl, isopropyl, butyl, or benzyl. Alternately, $R^1$ can be either methyl or ethyl.

In further embodiments in which Ar is the 4'-trifluoromethyl, 1,1'-biphenyl moiety, X is Y is and $R^1$ is H, methyl, ethyl, propyl, isopropyl, butyl, or benzyl.

In a number of embodiments of the compounds of formula I, Ar as a biphenyl group according to formula II and X is piperazine. In some of these embodiments, $R^5$ is CN, methyl, or hydrogen, Y is and $R^1$ is H, methyl, ethyl, propyl, isopropyl, butyl, or benzyl.

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Cancer Treatment using the Compounds of the Invention

The present invention provides methods for treating or preventing the development of cancer in a subject by administering to the subject a pharmaceutical composition including a compound of formula I or a pharmaceutically acceptable salt thereof. Cancer is a disease of abnormal and excessive cell proliferation. Cancer is generally initiated by an environmental insult or error in replication that allows a small fraction of cells to escape the normal controls on proliferation and increase their number. The damage or error generally affects the DNA encoding cell cycle checkpoint controls, or related aspects of cell growth control such as tumor suppressor genes. As this fraction of cells proliferates, additional genetic variants may be generated, and if they provide growth advantages, will be selected in an evolutionary fashion. Cells that have developed growth advantages but have not yet become fully cancerous are referred to as precancerous cells. Cancer results in an increased number of cancer cells in a subject. These cells may form an abnormal mass of cells called a tumor, the cells of which are referred to as tumor cells. The overall amount of tumor cells in the body of a subject is referred to as the tumor load. Tumors can be either benign or malignant. A benign tumor contains cells that are proliferating but remain at a specific site and are often encapsulated. The cells of a malignant tumor, on the other hand, can invade and destroy nearby tissue and spread to other parts of the body through a process referred to as metastasis.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system. Examples of types of cancer that can be treated using the compounds of the present invention include cancer is selected from the group consisting of leukemia, non-small cell lung cancer, colon cancer, central nervous system cancer, melanoma, ovarian cancer, renal cancer, prostate cancer, and breast cancer.

Cancer can be treated or prevented by regulating signaling pathways within the cancerous or potentially cancerous cells to prevent excessive growth or provide regulation of other aberrant processes within the cells. While not intending to be bound by theory, the compounds of the present invention can treat or prevent cancer by providing regulation of the Akt signaling pathway. The Akt signaling pathway includes enzymes that are members of the serine/threonine-specific protein kinase family, and are involved in cellular survival pathways, by, for example, inhibiting apoptotic processes. Activation of Akt requires phosphorylation at two amino acid residues, one of which is the phosphoinositide-dependent kinase 2 (PDK2) site. Integrin-linked kinase (ILK) is one of the kinases identified as being able to phosphorylated the PDK2 site. As demonstrated in the Examples provided herein, compounds of the present invention are capable of preventing PDK2 phosphorylation as a result of inhibiting integrin-linked kinase, and thereby decreasing the activation of Akt. Accordingly, one aspect of the present invention provides a method of inhibiting integrin-linked kinase in a cell by contacting the cell with a compound of formula I or a pharmaceutically acceptable salt thereof. The cell can be contacted in vivo, in vitro, or ex vivo. In some embodiments, the contacted cell can be a cancer cell.

The compounds of the invention can be used to provide prophylactic and/or therapeutic treatment. The compounds of the invention can, for example, be administered prophylactically to a subject in advance of the occurrence of cancer. Prophylactic (i.e., preventive) administration is effective to decrease the likelihood of the subsequent occurrence of cancer in the subject, or decrease the severity of cancer that subsequently occurs. Prophylactic treatment may be provided to a subject that is at elevated risk of developing cancer, such as a subject with a family history of cancer or exposure to high levels of carcinogens. Alternatively, the compounds of the invention can, for example, be administered therapeutically to a subject that is already afflicted by cancer. In one embodiment of therapeutic administration, administration of the compounds is effective to eliminate the cancer; in another embodiment, administration of the compounds is effective to decrease the severity of the cancer or lengthen the lifespan of the subject so afflicted. The subject is preferably a mammal, such as a domesticated farm animal (e.g., cow, horse, pig) or pet (e.g., dog, cat). More preferably, the subject is a human.

Administration and Formulation of the Compounds of the Invention

The present invention also provides pharmaceutical compositions that include compounds such as those defined by formula I as an active ingredient, and a pharmaceutically acceptable liquid or solid carrier or carriers, in combination with the active ingredient. Any of the compounds described above as being suitable for the treatment of cancer can be included in pharmaceutical compositions of the invention.

The compounds can be administered as pharmaceutically acceptable salts. Pharmaceutically acceptable salt refers to the relatively non-toxic, inorganic and organic acid addition salts of the compounds. These salts can be prepared in situ during the final isolation and purification of the compounds of the invention, or by separately reacting a purified compound of the invention with a suitable counterion, depending on the nature of the compound, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions include one or more compounds of the invention together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the compound, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The formulated compounds can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the active compound, or as a solution or suspension in an aqueous liquor or non-aqueous liquid such as a syrup, an elixir, an emulsion, or a draught. Such compositions and preparations typically contain at least about 0.1 wt-% of the active agent. The amount of the compound of the invention (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

Preparation of Compounds of Formula I

Figure 1A:
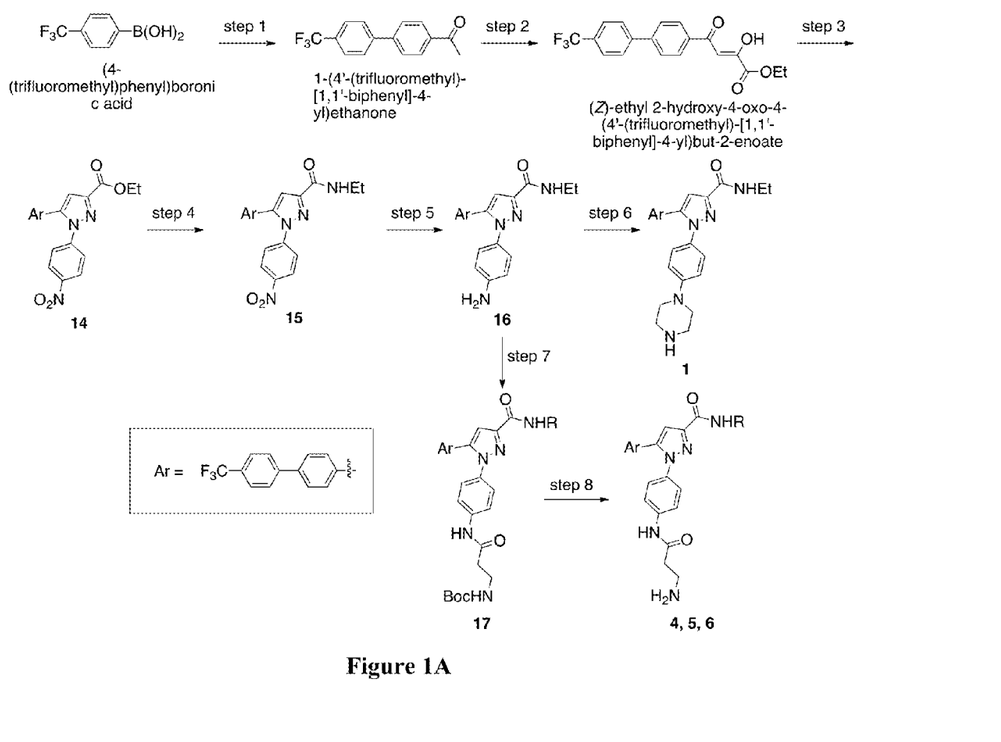
FIG. 1 provides a scheme showing the synthesis of compound 1-13.
Figure 1B:
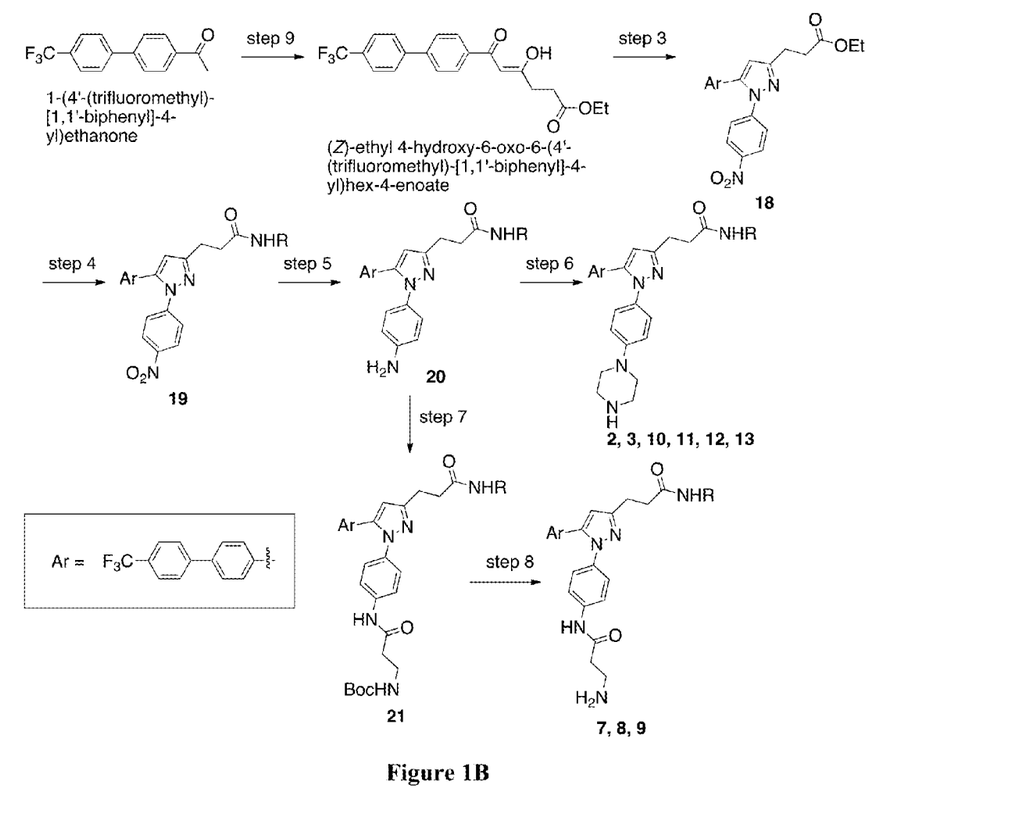

A general route for the preparation of compounds of the invention is shown in FIG. 1.

Synthesis of the 1-(4'-(trifluoromethyl)-[1,1'-biphenyl]-4-yl)ethanone precursor is shown in step 1 of FIG. 1. The mixture of 4-bromoacetophenone (11.8 g, 59 mmol), trichloromethyl phenylboronic acid (11.4 g, 60 mmol), palladium (II) acetate (250 mg, 2 mol %), powder potassium carbonate (20.3 g, 147 mmol), and tetrabutylammonium bromide (20.1 g, 62 mmol), was flushed with argon, and water (500 mL) was introduced with syringe. The resulting suspension was stirred and heated to 60° C. for 2 hours, then cooled to room temperature, diluted with water, extracted with ethyl acetate, dried over $Na_2SO_4$ and concentrated to dryness under vacuum to give the product (light yellow solid; 15.6 g, quantitative yield). The product was used without further purification in step 2.

Synthesis of the (Z)-ethyl 2-hydroxy-4-oxo-4-(4'-(trifluoromethyl)-[1,1'-biphenyl]-4-yl)but-2-enoate precursor is shown in step 2. To a suspension of sodium hydride (60% in mineral oil; 6.3 g, 157 mmol) in 100 mL of anhydrous tetrahydrofurane (THF) was added ethyl oxalate (14.4 g, 99 mmol) under argon. After stirring at room temperature (RT) for 10 minutes, 1-(4'-(trifluoromethyl)-[1,1'-biphenyl]-4-yl)ethanone (13.7 g, 52 mmol) in 50 mL of tetrahydrofurane solution was added drop wise to the solution. The mixture became clear and dark red within 30 minutes at RT. The mixture was then concentrated under vacuum and suspended in water, neutralized with hydrochloric acid (2N), the mixture became bright yellow suspension. Filter the mixture through vacuum to give product (yellow solid; 18.5 g, quantitative yield). The product was used without further purification in step 3.

The synthesis of the ethyl 1-(4-nitrophenyl)-5-(4'-(trifluoromethyl)-[1,1'-biphenyl]-4-yl)-1H-pyrazole-3-carboxylate (14) was carried out as shown in step 3. To a suspension of (Z)-ethyl 2-hydroxy-4-oxo-4-(4'-(trifluoromethyl)-[1,1'-biphenyl]-4-yl)but-2-enoate (10 g, 27 mmol) in 200 mL of ethanol was added 4-nitro-phenylhydrazine hydrochloride (5 g, 33 mmol). After stirring at RT for 16 hours, the mixture became dark brown solution with brown suspension. Concentrate the solution via vacuum, and recrystallized with ethanol to give product (brown solid; 8.2 g, 63%). The product was used without further purification in step 4.

The synthesis of the N-ethyl-1-(4-nitrophenyl)-5-(4'-(trifluoromethyl)-[1,1'-biphenyl]-4-yl)-1H-pyrazole-3-carboxamide (15) was carried out as shown in step 4. To a suspension of compound 14 (218 mg, 0.45 mmol) in 5 mL of ethanol was added ethylamine (70% in methanol, 5 mL). Transfer the mixture solution inside a seal tube, degas and seal the bottle. The bottle was heated to 120° C. and stirred for 16 hours. The reaction mixture turned into black solution with a yellow suspension. After the heating, remove the solvent under vacuum, and recrystallize with ethanol to give product (yellow solid; 153 mg, 70%).

The synthesis of the 1-(4-aminophenyl)-N-ethyl-5-(4'-(trifluoromethyl)-[1,1'-biphenyl]-4-yl)-1H-pyrazole-3-carboxamide (16) was carried out as shown in step 5 of FIG. 1. To a solution of compound 15 (153 mg, 0.32 mmol) in 20 mL of methanol was added palladium on activated charcoal (Pd/C; 15 mg), stirred under $H_2$ at 70 psi for 12 hours. The solution was then filtered through Celite filter pad to remove the catalyst, and concentrated to dryness under vacuum. The crude product was then recrystallized by chloroform to yield the product (white solid; 130 mg, 91%).

The synthesis of N-methyl-3-(1-(4-(piperazin-1-yl)phenyl)-5-(4'-(trifluoromethyl)-[1,1'-biphenyl]-4-yl)-1H-pyrazol-3-yl)propanamide (2) was carried out as shown in step 6. To a suspension of compound 20 (2 g, 4.3 mmol) in 20 mL of xylene was added bis(2-chloroethyl)amine hydrochloride (1053 mg, 5.9 mmol), after which the mixture was heated to 170° C. After stirring for 20 hours, the solution became brown sticky mixture. The solvent was removed using a vacuum, and the crude product was purified by silica gel chromatography, followed by recrystallization with ethyl acetate to give the product (white solid; 1334 mg, 58%).

The synthesis of the 1-(4-(3-aminopropanamido)phenyl)-N-methyl-5-(4'-(trifluoromethyl)-[1,1'-biphenyl]-4-yl)-1H-pyrazole-3-carboxamide (4) was carried out as shown in steps 7 and 8. To a solution of compound 16 (95 mg, 0.21 mmol) in 15 mL anhydrous tetrahydrofurane was added β-Ala-OH (111 mg, 0.59 mmol) and 1-ethyl-3-(3-dimethylaminopropyl)carbodiimide (EDC, 248 mg, 1.6 mmol). The mixture was then stirred at RT for 16 hours and then concentrated to dryness under vacuum. The residue was suspended in water, and the product was extracted by dichloromethane. The organic phase was dried over sodium sulfate, and concentrated to dryness under vacuum to give compound 17 (61 mg, 47%). Compound 17 (61 mg, 0.1 mmol) was dissolved in 10 mL of hydrochloride methanol solution (3N, 41 mL), stirred at RT for 2 hours, and concentrated to dryness under vacuum. The crude product was purified by silica gel chromatography to give compound 4 as a white powder (59 mg, quantitative yield).

The synthesis of the (Z)-ethyl 4-hydroxy-6-oxo-6-(4'-(trifluoromethyl)-[1,1'-biphenyl]-4-yl)hex-4-enoate precursor was carried out as shown in step 9. To a solution of 1-(4'-(trifluoromethyl)-[1,1'-biphenyl]-4-yl)ethanone (17 g, 64 mmol) in 500 mL of dichloromethane was added pre-prepared ethyl 4-(1H-benzo[d][1,2,3]triazol-1-yl)-4-oxobutanoate (19.8 g, 80 mmol), magnesium bromide ethyl etherate (22 g, 85 mmol) under argon. After stirring at RT for 10 minutes, N,N-Diisopropylethylamine (DIPEA, 20 ml, 115 mmol)) was added drop wise to the solution under argon. After stirring at RT for 16 hours, and washed with water (200 mL×2). The organic phase was dried over sodium sulfate, and concentrated to dryness under vacuum. The crude product was then purified by silica gel chromatography, followed by recrystallization with ethanol to give the product (white crystal; 20.9 g, 83%).

A number of additional compounds were prepared using the methods described above. Note that the Ar group can readily be varied from that shown in FIG. 1 using techniques known to those skilled in the art. The names and associated $^1$H NMR (proton nuclear magnetic resonance) and high resolution mass spectrometry data for these additional compounds are provided below.

N-ethyl-1-(4-(piperazin-1-yl)phenyl)-5-(4'-(trifluoromethyl)-[1,1'-biphenyl]-4-yl)-1H-pyrazole-3-carboxamide (1): $^1$H-NMR δ7.69 (s, 4H), 7.55 (d, J=7.8 Hz, 2H), 7.35 (d, J=7.9 Hz, 2H), 7.23 (d, J=8.4 Hz, 2H), 7.10 (s, 1H), 7.00 (t, J=5.4 Hz, 1H), 6.92 (d, J=8.6 Hz, 1H), 3.51 (m, 2H), 3.20 (m, 4H), 3.05 (m, 4H), 1.26 (t, J=7.1 Hz, 3H); $C_{29}H_{28}F_3N_5O$: HRMS (M+H$^+$): theoretical mass, 520.2324; actual mass, 520.2312

N-methyl-3-(1-(4-(piperazin-1-yl)phenyl)-5-(4'-(trifluoromethyl)-[1,1'-biphenyl]-4-yl)-1H-pyrazol-3-yl)propanamide (2): $^1$H-NMR δ7.93 (d, J=8.3 Hz, 2H), 7.71 (q, J=8.6 Hz, 4H), 7.64 (d, J=8.3 Hz, 2H), 7.35 (d, J=8.8 Hz, 2H), 6.98 (d, J=8.9 Hz, 2H), 6.54 (s, 1H), 5.54 (s, 1H), 3.21 (dd, J=6.2, 3.6 Hz, 4H), 3.06 (m, 4H), 3.01 (d, J=8.0 Hz, 2H), 2.78 (d, J=4.8 Hz, 3H), 2.45 (t, J=7.6 Hz, 2H); $C_{30}H_{30}F_3N_5O$: HRMS (M+H$^+$): theoretical mass, 534.2481; actual mass, 534.2467

N-ethyl-3-(1-(4-(piperazin-1-yl)phenyl)-5-(4'-(trifluoromethyl)-[1,1'-biphenyl]-4-yl)-1H-pyrazol-3-yl)propanamide (3); $^1$H-NMR δ7.93 (d, J=8.3 Hz, 2H), 7.71 (q, J=8.6 Hz, 4H), 7.63 (d, J=8.3 Hz, 2H), 7.35 (d, J=8.8 Hz, 2H), 6.98 (d, J=8.9 Hz, 2H), 6.54 (s, 1H), 5.53 (s, 1H), 3.28 (m, 3H), 3.20 (m, 4H), 3.03 (m, 6H), 2.44 (t, J=7.7 Hz, 2H), 1.10 (t, J=7.3 Hz, 3H); $C_{31}H_{32}F_3N_5O$: HRMS (M+H$^+$): theoretical mass 548.2637; actual mass, 548.2623

1-(4-(3-aminopropanamido)phenyl)-N-methyl-5-(4'-(trifluoromethyl)-[1,1'-biphenyl]-4-yl)-1H-pyrazole-3-carboxamide (4): $^1$H-NMR δ7.80 (d, J=8.0 Hz, 2H), 7.68 (m, 6H), 7.33 (m, 4H), 7.02 (s, 1H), 3.26 (d, J=5.7 Hz, 2H), 2.93 (s, 3H), 2.84 (t, J=5.6 Hz, 2H); $C_{27}H_{24}F_3N_5O_2$: HRMS (M+H$^+$): theoretical mass 508.1960; actual mass, 508.1953

1-(4-(3-aminopropanamido)phenyl)-N-ethyl-5-(4'-(trifluoromethyl)-[1,1'-biphenyl]-4-yl)-1H-pyrazole-3-carboxamide (5): $^1$H-NMR δ7.81 (d, J=8.2 Hz, 2H), 7.76-7.62 (m, 6H), 7.41-7.29 (m, 4H), 7.04 (s, 1H), 3.43 (dd, J=14.1, 7.0 Hz, 2H), 3.23 (m, 2H), 2.82 (t, J=6.0 Hz, 2H), 1.23 (t, J=7.1 Hz, 3H); $C_{28}H_{26}F_3N_5O_2$: HRMS (M+H$^+$): theoretical mass, 522.2117; actual mass, 522.2112

1-(4-(3-aminopropanamido)phenyl)-N-isopropyl-5-(4'-(trifluoromethyl)-[1,1'-biphenyl]-4-yl)-1H-pyrazole-3-carboxamide (6); ($^1$H-NMR data not available); $C_{29}H_{28}F_3N_5O_2$: HRMS (M+H$^+$): theoretical mass, 536.2273; actual mass, 536.2269.

3-amino-N-(4-(3-(3-(methylamino)-3-oxopropyl)-5-(4'-(trifluoromethyl)-[1,1'-biphenyl]-4-yl)-1H-pyrazol-1-yl)phenyl)propanamide (7): $^1$H-NMR δ7.86 (m, 4H), 7.73 (m, 4H), 7.19 (d, J=8.5 Hz, 2H), 6.82 (d, J=8.3 Hz, 2H), 6.66 (s, 1H), 3.48 (m, 2H), 3.30 (m, 2H), 3.98 (m, 2H), 2.69 (s, 3H), 2.51 (dd, J=10.0, 5.6 Hz, 2H); $C_{29}H_{28}F_3N_5O_2$: HRMS (M+H$^+$): theoretical mass, 536.2273; actual mass, 536.2269.

3-amino-N-(4-(3-(3-(ethylamino)-3-oxopropyl)-5-(4'-(trifluoromethyl)-[1,1'-biphenyl]-4-yl)-1H-pyrazol-1-yl)phenyl)propanamide (8): $^1$H-NMR δ7.92 (d, J=8.4 Hz, 2H), 7.84 (t, J=7.1 Hz, 4H), 7.74 (d, J=8.3 Hz, 4H), 7.50 (d, J=8.5 Hz, 2H), 6.74 (s, 1H), 3.30 (m, 2H), 3.18 (m, 2H), 2.97 (t, J=7.3 Hz, 2H), 2.88 (t, J=6.3 Hz, 2H), 2.54 (t, J=7.4 Hz, 2H), 1.08 (t, J=7.3 Hz, 3H); $C_{30}H_{30}F_3N_5O_2$: HRMS (M+H$^+$): theoretical mass, 550.2430; actual mass, 550.2429

3-amino-N-(4-(3-(3-(isopropylamino)-3-oxopropyl)-5-(4'-(trifluoromethyl)-[1,1'-biphenyl]-4-yl)-1H-pyrazol-1-yl)phenyl)propanamide (9): $^1$H-NMR δ7.95 (d, J=8.5 Hz, 2H), 7.87 (t, J=7.4 Hz, 4H), 7.77 (d, J=8.1 Hz, 4H), 7.53 (d, J=8.7 Hz, 2H), 6.77 (s, 1H), 4.95 (m, 1H), 2.99 (m, 2H), 2.91 (m, 2H), 2.56 (m, 2H), 1.12 (d, J=6.6 Hz, 6H); $C_{31}H_{32}F_3N_5O_2$: HRMS (M+H$^+$): theoretical mass, 564.2586; actual mass, 564.2579.

3-(5-(4'-cyano-[1,1'-biphenyl]-4-yl)-1-(4-(piperazin-1-yl)phenyl)-1H-pyrazol-3-yl)-N-methylpropanamide (10): $^1$H-NMR δ7.95 (d, J=8.4 Hz, 2H), 7.73 (m, 4H), 7.63 (d, J=8.4 Hz, 2H), 7.37 (d, J=8.7 Hz, 2H), 7.00 (d, J=8.8 Hz, 2H), 6.55 (s, 1H), 5.45 (bs, 1H), 3.27-3.18 (m, 4H), 3.07 (dd, J=3.9, 1.9 Hz, 4H), 3.02 (d, J=8.2 Hz, 2H), 2.80 (d, J=4.7 Hz, 3H), 2.47 (t, J=7.5 Hz, 2H); $C_{30}H_{30}N_6O$.

N-methyl-3-(5-(4'-methyl-[1,1'-biphenyl]-4-yl)-1-(4-(piperazin-1-yl)phenyl)-1H-pyrazol-3-yl)propanamide (11): $^1$H-NMR δ7.89 (d, J=8.3 Hz, 2H), 7.62 (d, J=8.3 Hz, 2H), 7.54 (d, J=7.9 Hz, 2H), 7.36 (d, J=8.9 Hz, 2H), 7.24 (m, 2H), 6.99 (d, J=8.8 Hz, 2H), 6.52 (s, 1H), 5.46 (s, 1H), 3.22 (m, 4H), 3.07 (dd, J=8.6, 4.4 Hz, 4H), 3.01 (d, J=8.3 Hz, 2H), 2.79 (d, J=4.8 Hz, 3H), 2.46 (m, 2H), 2.40 (s, 3H); $C_{30}H_{33}N_5O$ 3-(5-([1,1'-biphenyl]-4-yl)-1-(4-(piperazin-1-yl)phenyl)-1H-pyrazol-3-yl)-N-methylpropanamide (12): $^1$H-NMR δ7.91 (d, J=8.3 Hz, 2H), 7.64 (d, J=7.5 Hz, 4H), 7.45 (t, J=7.4 Hz, 2H), 7.36 (d, J=8.3 Hz, 3H), 6.99 (d, J=8.6 Hz, 2H), 6.53 (s, 1H), 5.48 (s, 1H), 3.23 (m, 4H), 3.08 (m, 4H), 3.01 (d, J=8.2 Hz, 2H), 2.79 (d, J=4.7 Hz, 3H), 2.46 (t, J=7.6 Hz, 2H); $C_{29}H_{31}N_5O$ N-methyl-3-(5-(phenanthren-2-yl)-1-(4-(piperazin-1-yl)phenyl)-1H-pyrazol-3-yl)propanamide (13): $^1$H-NMR δ8.71 (dd, J=4.8, 3.7 Hz, 2H), 8.35 (m, 1H), 8.16 (dd, J=8.4, 0.8 Hz, 1H), 7.89 (d, J=7.7 Hz, 1H), 7.76 (q, J=8.7 Hz, 2H), 7.63 (m, 2H), 7.39 (d, J=8.6 Hz, 2H), 7.00 (d, J=8.6 Hz, 2H), 6.67 (s, 1H), 5.49 (bs, 1H), 3.21 (m, 4H), 3.05 (m, 6H), 2.80 (d, J=4.6 Hz, 3H), 2.49 (t, J=7.5 Hz, 2H); $C_{31}H_{31}N_5O$ Example 2

Pharmacology of Compounds 1-13

Figure 2:
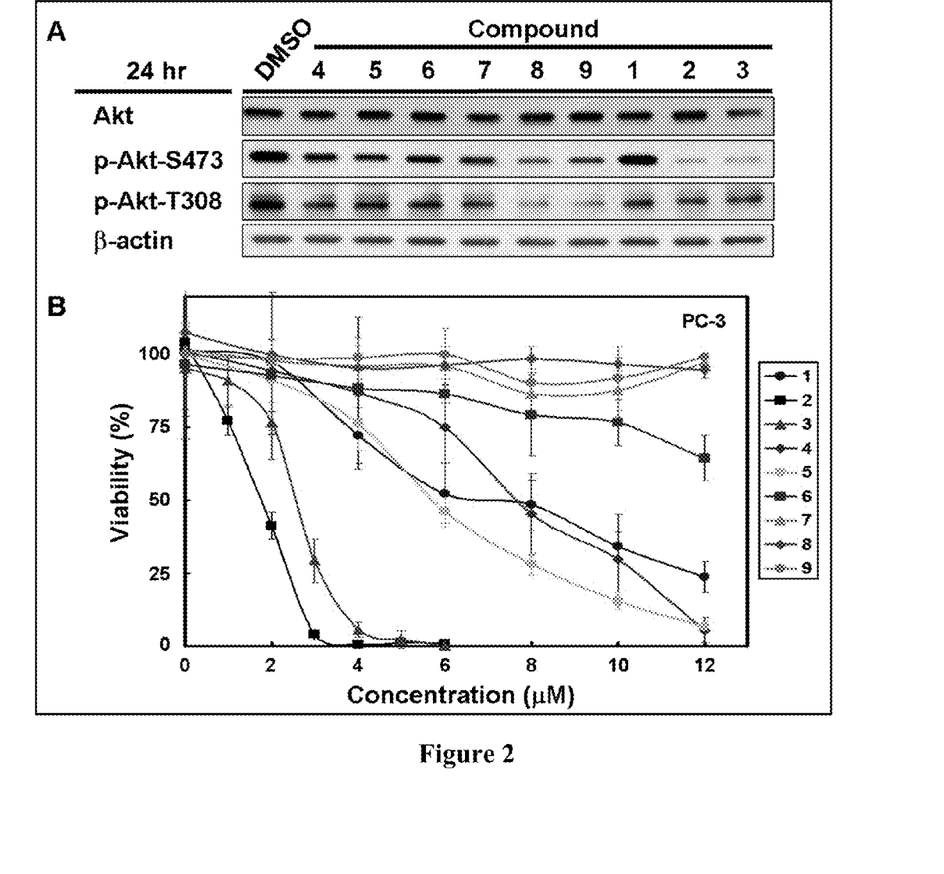
FIG. 2 provides (A) Western blot analysis of the effects of compounds 1-9 on Akt phosphorylation at the PDK1 (T308) and PDK2 (S473) sites in PC-3 human prostate cancer cells after 24 h treatment at 2.5 µM in the presence of 5% fetal bovine serum (FBS), and (B) Dose-dependent effects of compounds 1-9 on the viability of PC-3 cells treated as described above in A. Cell viability was assessed by MTT assay. Points, mean; bars, ±SD.

Compounds 1-9 were screened for (a) evidence of PDK2 inhibitory activity (i.e. the ability to selectively inhibit Akt phosphorylation at the PDK2 site [S473] versus the PDK1 site [T308]), and (b) antiproliferative activity by Western blot analysis and MTT assays, respectively, in PC-3 human prostate cancer cells. As shown in FIG. 2A, two of the screened compounds (2 and 3) induced a marked selective inhibition of Akt-S473 phosphorylation, indicating PDK2 inhibitory activity. Moreover, compounds 2 and 3 were also the most potent among the nine compounds with respect antiproliferative activity (FIG. 2B).

Figure 3:
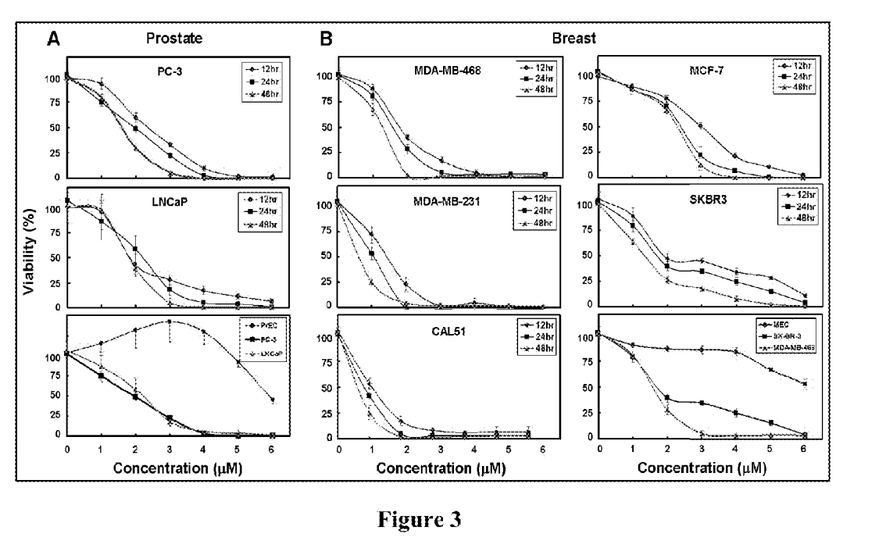
FIG. 3 shows the antiproliferative effects of compound 2 in a panel of prostate and breast cancer cells lines and nonmalignant prostate and mammary epithelial cells. Time- and/or dose-dependent effects of compound 2 on cell viability in (A) prostate cancer (PC-3, LNCaP) and nonmalignant prostate epithelial cells (PrEC), and (B) breast cancer (MDA-MB-468, MDA-MB-231, CAL51, MCF-7, SKBR3) and nonmalignant mammary epithelial cells (MEC) were determined. Cells were treated for 12, 24 or 48 h at the indicated concentrations and cell viability determined by MTT assays. Points, mean; bars, ±SD.

As structurally related compounds 2 and 3 differ only in that the N-alkyl moiety, i.e., methyl versus ethyl, compound 2 was selected for more thorough evaluation. Dose- and time-dependent effects of compound 2 on cell viability were determined in a panel of two prostate (PC-3, LNCaP) and five breast cancer (MDA-MB-468, MDA-MB-231, CAL51, MCF-7, SKBR3) cell lines (FIGS. 3A and B). Moreover, cancer cell lines were also evaluated in parallel with nonmalignant prostate and mammary epithelial cells (FIG. 3A, lower panel; 3B lower right panel). Importantly, compound 2 exhibited selective cytotoxicity for cancer cells versus their nonmalignant counterparts.

The data indicate that compound 2 is a putative inhibitor of integrin-linked kinase. Complete activation of Akt requires phosphorylation at two amino acid residues: T302 which is phosphorylated by phosphoinositide-dependent protein kinase-1 (PDK1), and S473 which is known as the PDK2 site and can be phosphorylated by a number of different kinases. One of these, integrin-linked kinase (ILK), has been identified as a promising anti-cancer target as its expression and activity are increased in various types of cancer, and its inhibition can suppress cancer cell survival by inducing apoptosis and cell-cycle arrest.

Figure 4:
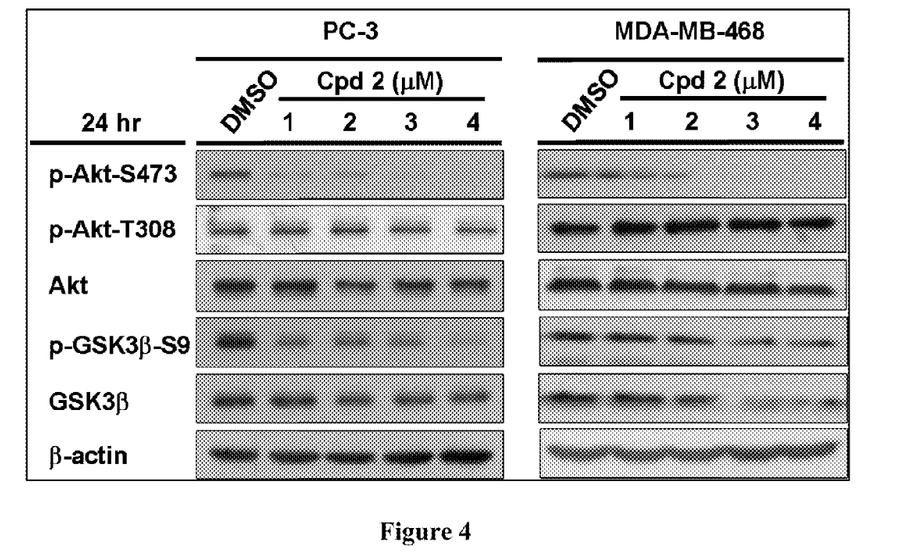
FIG. 4 provides evidence that Compound 2 suppresses the ILK signaling pathway. Western blot analysis of the dose-dependent effect of Compound 2 on downstream targets of ILK (Akt-S473; GSK3β-S9) in PC-3 and MDA-MB-231 cells. Cells were treated for 24 h at the indicated concentrations in the presence of 5% FBS.

Based on western blot data showing the selective reduction in phospho-Akt-S473 levels relative to those of phospho-Akt-T308 (FIG. 2A), compound 2 was identified as an inhibitor of PDK2 activity. To evaluate compound 2 for the ability to inhibit ILK signaling, its effect on downstream targets of ILK was assessed in PC-3 and MDA-MB-468 cells by Western blotting (FIG. 4). In addition to causing a marked and selective decrease in phospho-S473-Akt levels, compound 2 also reduced the phosphorylation of another ILK substrate, GSK3β, suggesting that compound 2 is an inhibitor of ILK.

Figure 5:
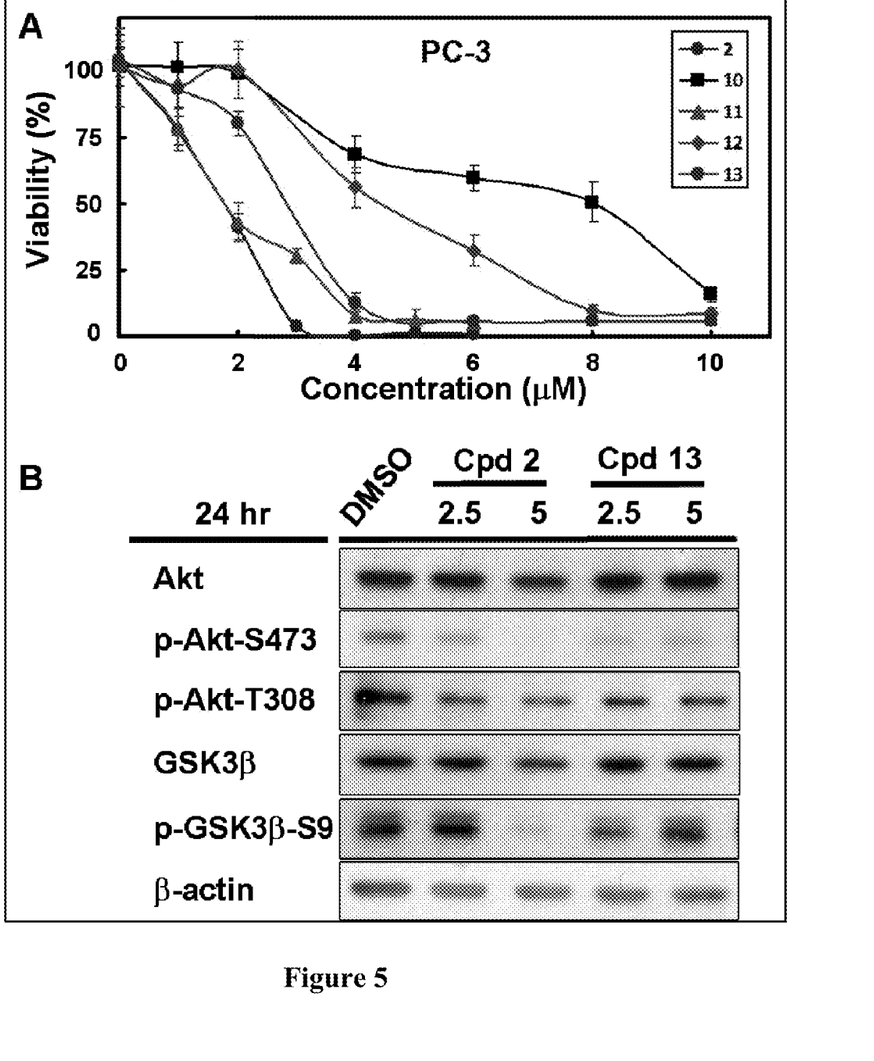
FIG. 5 provides the results from the screening of compounds 10-13. (A) Dose-dependent effects of compounds 10-13 and 2 on the viability of PC-3 cells after 24 h treatment at 2.5 µM in the presence of 5% FBS. Cell viability was assessed by MTT assay. Points, mean; bars, ±SD. (B) Western blot analysis of the effects of compounds 2 and 13 on the phosphorylation status of downstream targets of ILK in PC-3 cells.

In another series of tests, Compounds 10-13 were screened for antiproliferative activity, in parallel with compound 2, by MTT assay in PC-3 human prostate cancer cells. As shown in FIG. 5A, compounds 11 and 13 exhibited the highest potencies with $IC_{50}$ values in the 2-3 μM range, though neither exceeded that of compound 2. The effects of compound 13, vs. compound 2, on the phosphorylation status of downstream targets of ILK in PC-3 cells were evaluated by western blotting. Compound 13 induced a strong reduction in phospho-Akt-S473 relative to phospho-Akt-T308, but, unlike compound 2, it did not exhibit substantial suppressive activity against GSK3β phosphorylation (FIG. 5B).

Figure 6:
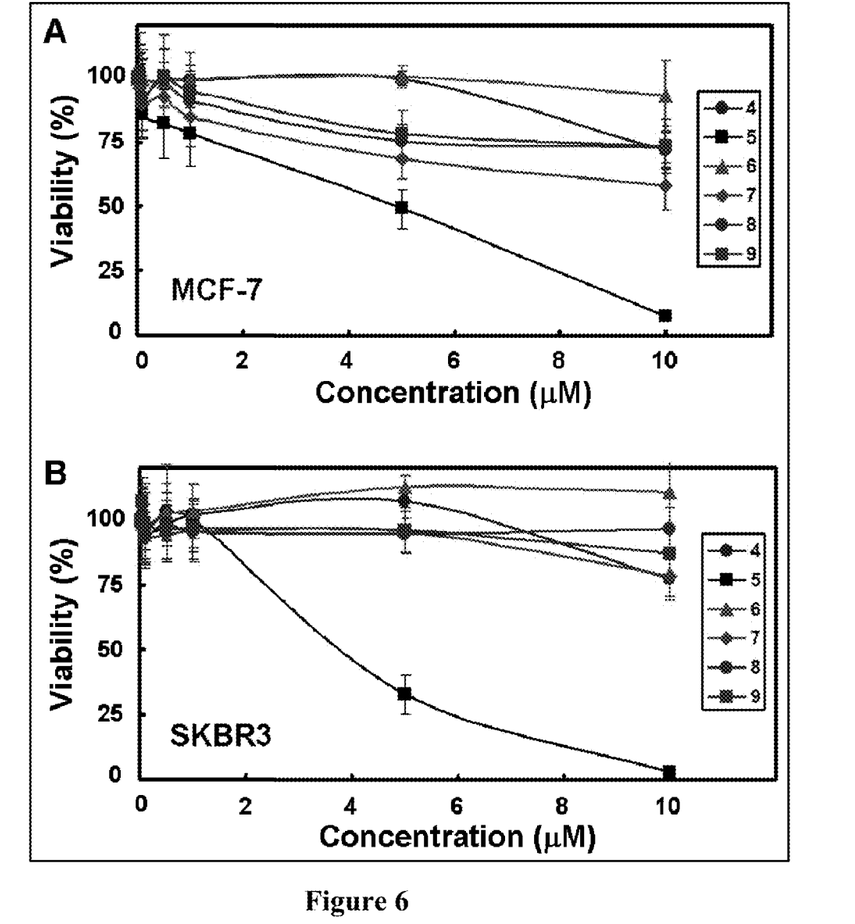
FIG. 6 shows the antiproliferative activity of compounds 4-9 in breast cancer cells. Dose-dependent effects of compounds 4-9 in MCF-7 (upper panel) and SKBR3 (lower) cells after 24 h treatment in the presence of 5% FBS. Cell viability was assessed by MTT assay. Points, mean; bars, ±SD.

Compounds 4-9, which were screened previously in a prostate cancer cell line (FIG. 2), were evaluated for antiproliferative activity in MCF-7 and SKBR3 human breast cancer cells. While compound 5 was the only compound among those tested that showed activity in either cell line ($IC_{50}$ values in the 4-5 μM range) (FIG. 6), it was less potent than compound 2 was shown to be in these same cell lines (FIG. 3B).

Figure 7:
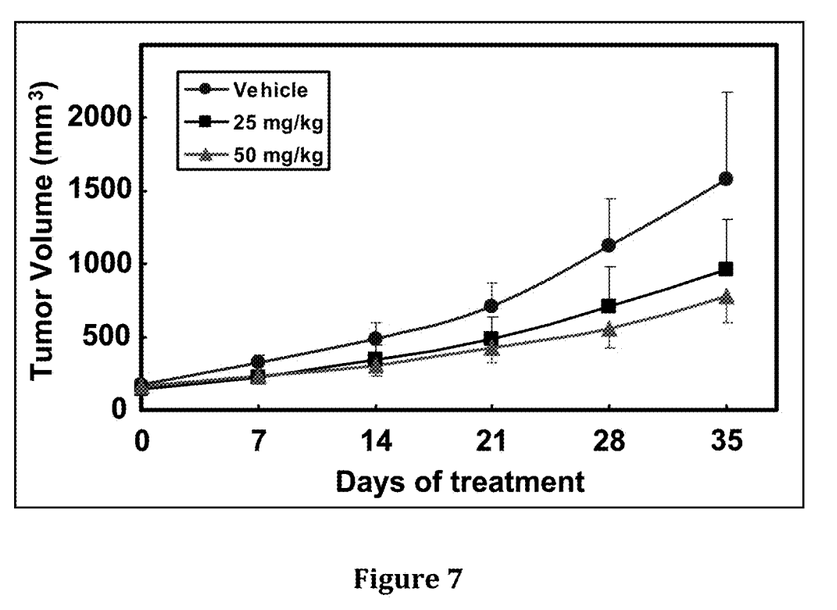
FIG. 7 shows the effect of oral administration of compound 2 on the growth of established PC-3 tumors in athymic nude mice. PC-3 tumors were established in male athymic nude mice by subcutaneous injection of 5×10⁵ PC-3 cells in a total volume of 0.1 ml serum-free medium containing 50% Matrigel. Mice with established tumors were randomized to three groups receiving the indicated treatments once daily by gavage for 35 days. Tumor sizes and body weights were measured weekly. Points, mean tumor volume; bars, ±SD.

The In vivo tumor suppressive activity of compound 2 in the PC-3 prostate tumor xenograft model was also evaluated. Based on the results described above, compound 2 was identified as the lead agent for development as a novel ILK/PDK2 inhibitor. To evaluate the in vivo antitumor activity of compound 2, athymic nude mice bearing established subcutaneous PC-3 tumor xenografts (mean starting tumor volume, 157.1±29.1 mm³) were treated orally for 35 days with compound 2 at 25 or 50 mg/kg once daily or with vehicle (0.5% methylcellulose and 0.1% Tween 80 in sterile water) (n=5 mice). As shown in FIG. 7, daily treatment of mice with compound 2 at 25 mg/kg and 50 mg/kg inhibited PC-3 tumor growth by 42% (P=0.10) and 56% (P=0.03), respectively, relative to vehicle-treated controls at 35 days of treatment. The in vivo efficacy of compound 2 after oral administration indicates its oral bioavailability. Moreover, the compound was well tolerated by the mice which exhibited no overt signs of toxicity, nor significant changes in body weight over the course of the study.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing possible mechanisms through with the compounds of the invention are effective, the inventors are not bound by theories described herein. The invention is not limited to the exact details shown and described, for variations obvious to one skilled in the art will be included within the invention defined by the claims.

What is claimed is:

1. A compound according to Formula I:

wherein Ar is a substituted or unsubstituted biphenyl group;

Y is selected from the group consisting of sulfonamide, wherein n is an integer from 0-3, $R^1$ is H, methyl, ethyl, propyl, i-propyl, or benzyl; and $R^2$ is H, methyl or ethyl; and X is wherein $R^4$ is H, methyl, ethyl, allyl, $CH_2CH_2OH$, or $CH_2CN$;

or pharmaceutically acceptable salts thereof.

2. The compound of claim 1 wherein Ar is a biphenyl group according to formula II wherein R⁵ is H, methyl, ethyl, propyl, isopropyl, tert-butyl, $CF_3$, $CCl_3$, hydroxyl, OMe, CN, $NO_2$, $NH_2$, $CONH_2$, CONHMe, acetate, $CO_2H$, $CO_2Me$, F, Cl, Br, or I.

3. The compound of claim 2 where R⁵ is $CF_3$.

4. The compound of claim 3, wherein X is piperazine, Y and R¹ is H, methyl, ethyl, propyl, isopropyl, butyl, or benzyl.

5. The compound of claim 3 wherein X is piperazine, Y is and R¹ is H, methyl, ethyl, propyl, isopropyl, butyl, or benzyl.

6. The compound of claim 5, wherein R¹ is methyl or ethyl.

7. The compound of claim 3 wherein X is

Y is and R¹ is H, methyl, ethyl, propyl, isopropyl, butyl, or benzyl.

8. The compound of claim 3 wherein X is

Y is and R¹ is H, methyl, ethyl, propyl, isopropyl, butyl, or benzyl.

9. The compound of claim 2 wherein R⁵ is CN, Y is and R¹ is H, methyl, ethyl, propyl, isopropyl, butyl, or benzyl.

10. The compound of claim 2 wherein R⁵ is methyl, Y is and R¹ is H, methyl, ethyl, propyl, isopropyl, butyl, or benzyl.

11. The compound of claim 2, wherein R⁵ is hydrogen, Y is and R¹ is H, methyl, ethyl, propyl, isopropyl, butyl, or benzyl.

12. A method for treating cancer in a subject, wherein the cancer is selected from the group consisting of leukemia, non-small cell lung cancer, colon cancer, melanoma, ovarian cancer, renal cancer, prostate cancer, and breast cancer, comprising administering to the subject a pharmaceutical composition including a compound of formula I or a pharmaceutically acceptable salt thereof, wherein Ar is a substituted or unsubstituted biphenyl group;

Y is selected from the group consisting of sulfonamide, and wherein n is an integer from 0-3, R¹ is H, methyl, ethyl, propyl, i-propyl, or benzyl; and R² is H, methyl or ethyl; and X is wherein
R$^4$ is methyl, ethyl, allyl, CH$_2$CH$_2$OH, or CH$_2$CN.

13. The method of claim 12, wherein X is piperazine, Y is and Ar is a biphenyl group according to formula II wherein R$^1$ is H, methyl, ethyl, propyl, isopropyl, butyl, or benzyl and R$^5$ is H, methyl, ethyl, propyl, isopropyl, tert-butyl, CF$_3$, CCl$_3$, hydroxyl, OMe, CN, NO$_2$, NH$_2$, CONH$_2$, CONHMe, acetate, CO$_2$H, CO$_2$Me, F, Cl, Br, or I.

14. The method of claim 13, wherein R$^1$ is methyl or ethyl and R$^5$ is CF$_3$.

15. A method of inhibiting integrin-linked kinase in a cell by contacting the cell with a compound of formula I or a pharmaceutically acceptable salt thereof, wherein Ar is a substituted or unsubstituted biphenyl group;
Y is selected from the group consisting of sulfonamide, wherein n is an integer from 0-3,
R$^1$ is H, methyl, ethyl, propyl, i-propyl, or benzyl; and R$^2$ is H, methyl or ethyl; and
X is wherein
R$^4$ is methyl, ethyl, allyl, CH$_2$CH$_2$OH, or CH$_2$CN.

16. The method of claim 15, wherein X is piperazine, Y is and Ar is a biphenyl group according to formula II wherein R$^1$ is H, methyl, ethyl, propyl, isopropyl, butyl, or benzyl and R$^5$ is H, methyl, ethyl, propyl, isopropyl, tert-butyl, CF$_3$, CCl$_3$, hydroxyl, OMe, CN, NO$_2$, NH$_2$, CONH$_2$, CONHMe, acetate, CO$_2$H, CO$_2$Me, F, Cl, Br, or I.

17. The method of claim 16, wherein R$^1$ is methyl or ethyl and R$^5$ is CF$_3$.

* * * * *